United States Patent [19]
Uribe

[11] Patent Number: 6,127,352
[45] Date of Patent: Oct. 3, 2000

[54] PHARMACEUTICAL COMPOSITIONS WITH ANALGESICS CONTAINING CODEINE

[76] Inventor: Jose R. Uribe, 24 Whitewood Dr., Morris Plains, N.J. 07950

[21] Appl. No.: 07/949,347

[22] Filed: Sep. 22, 1992

Related U.S. Application Data

[63] Continuation of application No. 07/834,480, Feb. 12, 1992, abandoned, which is a continuation-in-part of application No. 07/593,472, Oct. 2, 1990, abandoned, which is a continuation of application No. 07/427,013, Oct. 25, 1989, abandoned, which is a continuation of application No. 07/310,768, Feb. 14, 1989, abandoned, which is a continuation of application No. 07/151,023, Feb. 1, 1988, abandoned.

[51] Int. Cl.$^7$ .......................... A61K 31/60; A61K 31/44; A61K 31/16
[52] U.S. Cl. .......................... 514/159; 514/161; 514/163; 514/165; 514/282; 514/629
[58] Field of Search ..................................... 514/159, 282, 514/629, 161, 165, 163

[56] References Cited

U.S. PATENT DOCUMENTS 2,889,249   6/1959   Beiler et al. ............................. 514/282

OTHER PUBLICATIONS

Hertz et al. (Hertz), "Analgesic Effect of Acetaminophen–Codeine Combination in Mice," Drug Development Research, vol. 6, pp. 55–60 (1985).
Chemical Abstracts (78: 106205w) 1973.
Chemical Abstracts (103: 64783k) 1985.
Chemical Abstracts (103: 166191h) 1985.
Chemical Abstracts (105: 232456t) 1986.
*The Merck Index*, 10$^{th}$ Edition. 1985 Abstracts Nos. 39, 98 and 2423.

*Primary Examiner*—Kevin E. Weddington
*Attorney, Agent, or Firm*—Graham, Curtin & Sheridan; Richard T. Laughlin, Esq.

[57] ABSTRACT

Compositions for the relief of pain containing acetyl salicylic acid or acetaminophen as a peripherally acting analgesic and codeine as a centrally acting agent.

9 Claims, No Drawings

PHARMACEUTICAL COMPOSITIONS WITH ANALGESICS CONTAINING CODEINE

RELATED PATENT APPLICATIONS

This application is a continuation of application Ser. No. 07/834,480 filed Feb. 12, 1992 now abandoned which in turn was a continuation-in-part of application Ser. No. 07/593,472 filed Oct. 2, 1990 now abandoned, which in turn was a continuation of Ser. No. 07/427,013 filed Oct. 25, 1989 and now abandoned, which in turn was a continuation of Ser. No. 07/310,768 filed Feb. 14, 1989 now abandoned which in turn was a continuation of application Ser. No. 07/151,023 filed Feb. 1, 1988 and now abandoned.

This Invention relates to novel pharmaceutical compositions containing codeine and particularly to such compositions having reduced side effects while relieving pain with more efficiency.

BACKGROUND OF THE INVENTION

The analgesic compositions generally used for relieving a large variety of pain states contain two levels of codeine as the central acting agent and as the peripherally acting agent(s) acetaminophen or acetyl salicylic acid or combinations of these two agents. The most universal combinations come in two forms of either 30 or 60 mg of codeine with 300 mg of acetaminophen or 325 mg of acetyl salicylic acid. The most common composition contains the smaller amount of codeine since the larger the amount of codeine, the severer the side effects. It is the general belief that the smaller amount of codeine the less effective is the composition as an analgesic. However, there are compositions available with 300 mg of acetaminophen or acetyl salicylic acid and lower amounts of codeine such as 7.5 mg and 15 mg which are used for children or patients with small body weight. Nevertheless, over 99% of the use of "Codeine Combinations" consists of combinations including 30 or more mg of codeine, and the combination of 30 mg of codeine with 300 mg of acetaminophen represents about 90% of all usage of codeine combinations, reason for which we call it the "state of the art Codeine Combination".

U.S. Pat. No. 2,889,249 issued to Beiler et al. discloses a combination of codeine and aspirin with α-allyl-α-benzylacetamide. The most pertinent prior art is the combinations of codeine recited above.

OBJECTS OF THE INVENTION

It is a primary object of the invention to provide analgesic compositions which have lower amounts of codeine than the state of the art Codeine Combination, while maintaining the "Analgesic Performance", that is, the ratio of efficacy to side effects experienced by the patient.

Another object of the invention is to provide such a composition which can be readily administered either orally or rectally.

A further object of the invention is to provide such compositions which can be freely administered without concern for unexpected side effects.

DESCRIPTION OF THE INVENTION

In accordance with the invention it has been discovered that an effective analgesic having improved analgesic performance can be provided with low amounts of codeine if the amount of peripherally acting agent is substantially increased over what was heretofore used. This discovery is surprising since the undesirable side effects and possible addiction resulting from the use of larger quantities of codeine is well known and it would be assumed that compositions would utilize the smallest amount considered affective.

The peripheral acting agent is acetyl salicylic acid or acetaminophen or a combination of the two. When utilizing a combination, the range of acetyl salicylic acid would be from 10 to 80% by weight with the remainder, 20 to 90% being acetaminophen. The preferred composition contains 1000 mg of the peripheral acting agent in combination with 15 mg of codeine. The range of codeine utilized in the composition of the invention is from 7.5 to 20 mg with the 1000 mg of peripheral acting agent.

As a general rule, a patient would be given a regimen of one single dose every four to six hours. The dose can be divided and administered in two oral tablets, oral capsules or rectal suppositories.

The relief of pain is a subjective measurement which can vary very widely among patients. There is an assessment stated by the general public as one having a high or low threshold of pain. Although the utilization of average response of a patient to well being is a generally accepted standard, but for the individual patient, such generalities are unsuitable.

The effectiveness of the compositions of this invention have been shown by comparing the most currently used composition versus the compositions of this invention. It has been found that when comparing the analgesic performance of the state of the art composition, which consists of single doses of 300 mg acetaminophen with 30 mg codeine, versus the composition of this invention, consisting of single doses of 1000 mg of acetaminophen with 15 mg codeine, on the basis of the patients' evaluation of efficacy and side effects, the resulting ratio of efficacy to side effects of this invention is higher than that of the prior art. In one study with 156 patients the ratio of efficacy to side effects of the innovative combination was 66% better than that of the state of the art Codeine Combination. In a second study with 143 patients, the ratio of efficacy to side effects of the innovative combination was 78% better.

For administration, these compositions of the invention can be prepared in any of the standard unit dosage forms. Oral administration by the use of tablets and capsules is preferred. Said compositions are prepared in a conventional manner by the addition of suitable pharmaceutical carriers including fillers, diluents, lubricants and the like. When prepared in tablet form, the conventional binding and disintegrating agents are employed. Additional active ingredients compatible with the analgesic agents such as appropriate stimulants, sedatives or the like, to add other desirable properties to said compositions. The incorporation of said additives broadens the area of therapeutic utility of the present compositions, making them especially useful in particular cases where, in addition to anti-inflammatory, analgesic and antipyretic activity, other beneficial effects, such as stimulation, sedation, or the like, are desired.

The examples that follow are illustrative of a typical composition of the present invention prepared by conventional well known tableting techniques such as those disclosed in U.S. Pat. Nos. 3,018,221; 2,798,024 and 2,757,124 as a tablet for oral administration.

EXAMPLE 1

| INGREDIENT | MG |
|---|---|
| Acetyl salicylic acid | 1000.0 |
| Codeine | 15.0 |
| Hydroxypropyl Methylcellulose 2910 USP (15 cps) | 21.2 |
| Croscarmellose Sodium, NF, Type A | 44.6 |
| Microcrystalline Cellulose NF | 254.0 |

-continued

| INGREDIENT | MG |
|---|---|
| Sodium Metabisufite, NF | 2.12 |
| Polyvinyl pyrrolidone USP | 46.6 |
| D & C Yellow No. 10 Dye | 0.42 |
| Magnesium Stearate, NF | 12.72 |
| Stearic Acid NF, Powder, Food Grade | 9.12 |

A tablet is administered to a patient up to four times a day.

EXAMPLE 2

| INGREDIENT | COMPOSITION (mg) |
|---|---|
| Acetaminophen | 1000.0 |
| Codeine | 15.0 |
| Hydroxypropyl Methylcellulose 2910 USP (15 cps) | 21.2 |
| Croscarmellose Sodium, NF, Type A | 44.6 |
| Microcrystalline Cellulose NF | 254.0 |
| Sodium Metabisufite, NF | 2.12 |
| Polyvinyl pyrrolidone USP | 46.6 |
| D & C Yellow No. 10 Dye | 0.42 |
| Magnesium Stearate, NF | 12.72 |
| Stearic Acid NF, Powder, Food Grade | 18.24 |

A tablet is administered to a patient four times a day.

EXAMPLE 3

| INGREDIENT | COMPOSITION (mg) |
|---|---|
| Acetyl salicylic acid | 500.0 |
| Acetaminophen | 500.0 |
| Codeine | 20.0 |
| Hydroxypropyl Methylcellulose 2910 USP (15 cps) | 21.2 |
| Croscarmellose Sodium, NF, Type A | 44.6 |
| Microcrystalline Cellulose NF | 254.0 |
| Sodium Metabisufite, NF | 2.12 |
| Polyvinyl pyrrolidone USP | 46.6 |
| D & C Yellow No. 10 Dye | 0.42 |
| Magnesium Stearate, NF | 12.72 |
| Stearic Acid NF, Powder, Food Grade | 18.24 |

A tablet is administered to a patient four times a day.

Any departure from the foregoing description which conforms to the present invention is intended to be included within the scope of the claims.

What is claimed is:

1. A method for systematically treating and relieving pain which comprises orally administrating to a patient in need of treatment, a composition consisting of 1000 mg. of acetyl salicylic acid or acetaminophen, admixed with 7.5 to 20 mg of codeine as a centrally active agent.

2. The method as defined in claim 1 wherein the peripheral acting agent consists of from 10 to 80% by weight of acetyl salicylic acid and the remainder acetaminophen.

3. The method as defined in claim 1 where the peripheral acting agent consists of acetaminophen and the codeine utilized is 15 mg.

4. The method as defined in claim 1 wherein the peripheral acting agent consists of acetyl salicylic acid and the codeine utilized is 15 mg.

5. The method as defined in claim 1 wherein the peripheral acting agent consists of a mixture of equal parts of acetyl salicylic acid and acetaminophen, and the codeine utilized is 15 mg.

6. A therapeutic composition, in unit dosage form, for the systematic treatment and relief of pain, said composition consisting of about 1000 mg of a peripheral acting agent comprising acetyl salicylic acid, acetaminophen or a combination of 10 to 80% of acetyl salicylic acid and 20 to 90% of acetaminophen, and from 7.5 to 20 mg of codeine as a centrally active agent.

7. The composition as defined in claim 6 wherein the peripheral acting agent is acetaminophen and the codeine utilized is 15 mg.

8. The composition as defined in claim 6 where the peripheral acting agent is acetyl salicylic acid and the codeine utilized is 15 mg.

9. The composition as defined in claim 6 where the peripheral acting agent is a mixture of 50% acetyl salicylic acid and 50% acetaminophen and the codeine utilized is 15 mg.

* * * * *